Figure 1:
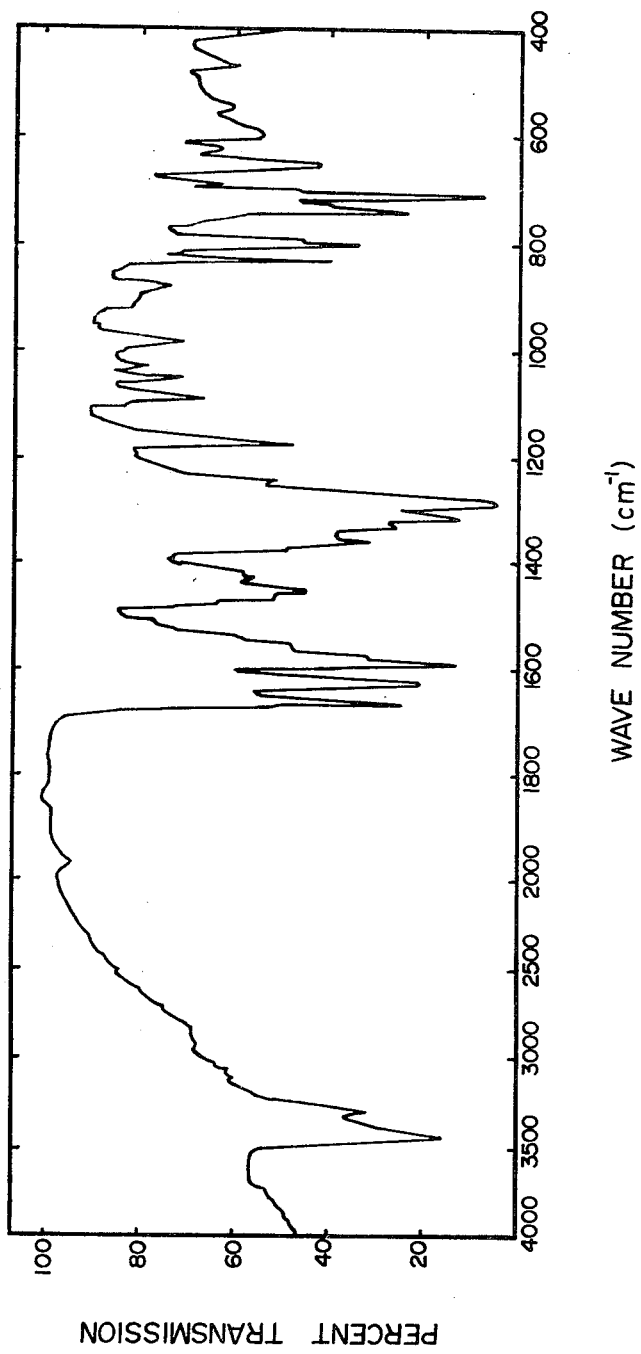

United States Patent

Fukui et al.

[11] 3,966,775
[45] June 29, 1976

[54] PROCESS FOR THE PREPARATION OF 1-SUBSTITUTED ANTHRAQUINONES

[75] Inventors: Akio Fukui, Kyoto; Hiroshi Koike, Takatsuki; Takehiko Tanaka, Kobe; Yuji Ito, Amagasaki, all of Japan

[73] Assignee: Nippon Shokubai Kagaku Kogyo Co., Ltd., Japan

[22] Filed: Oct. 25, 1974

[21] Appl. No.: 518,209

[30] Foreign Application Priority Data

| Oct. 26, 1973 | Japan | 48-119978 |
| Nov. 9, 1973 | Japan | 48-125422 |
| Jan. 9, 1974 | Japan | 49-5318 |
| Jan. 10, 1974 | Japan | 49-5626 |
| May 8, 1974 | Japan | 49-50276 |

[52] U.S. Cl. ............................ 260/378; 260/380
[51] Int. Cl.² ................... C07C 85/11; C07C 89/00
[58] Field of Search ................................. 260/378

[56] References Cited
UNITED STATES PATENTS

| 2,276,637 | 3/1942 | Zahn et al. | 260/378 X |
| 2,570,866 | 10/1951 | Sargent et al. | 260/378 X |
| 2,607,782 | 8/1952 | Seymour et al. | 260/378 |
| 3,417,090 | 12/1968 | Pelster et al. | 260/378 UX |

*Primary Examiner*—Allen B. Curtis
*Attorney, Agent, or Firm*—Armstrong, Nikaido & Wegner

[57] ABSTRACT

A process for the preparation of 1-substituted anthraquinones represented by the general formula I

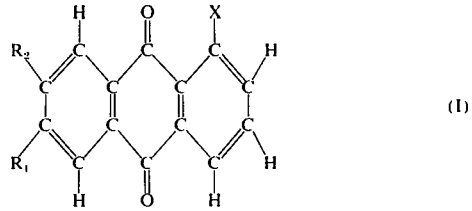

(I)

where, in the formula, $R_1$ and $R_2$ represent individually a hydrogen atom or methyl group and X represents a hydroxylamino or amino group, which comprises treating in a liquid medium a 5-nitro-1,4,4a,9a-tetrahydroanthraquinone represented by the general formula II

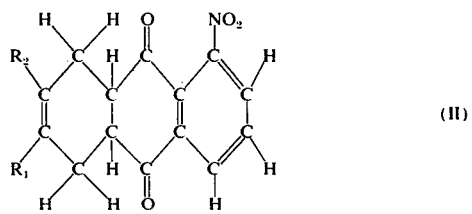

(II)

where, in the general formula, $R_1$ and $R_2$ represent individually a hydrogen atom or methyl group, in the presence of a basic compound with or without a reducing agent.

38 Claims, 2 Drawing Figures

PROCESS FOR THE PREPARATION OF 1-SUBSTITUTED ANTHRAQUINONES

This invention relates to a process for the preparation of 1-substituted anthraquinones and, more particularly, to a process for the preparation of 1-substituted anthraquinones represented by the following general formula I

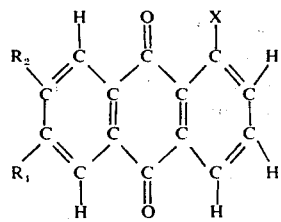

where, in the general formula, $R_1$ and $R_2$ represent individually a hydrogen atom or methyl group and X represents a hydroxylamino or amino group, from 5-nitro-1,4,4a, 9a-tetrahydroanthraquinones represented by the following general formula II

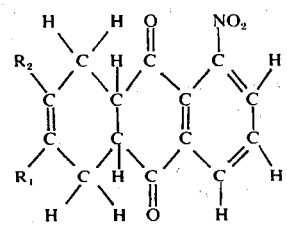

where, in the general formula, $R_1$ and $R_2$ represent individually a hydrogen atom or methyl group.

1-Hydroxylaminoanthraquinones and 1-aminoanthraquinones represented by the above general formula I are of great value as intermediates for dyes and pigments.

In the reduction of nitro compounds, in general, there are inevitably formed nitroso (—NO) compounds, azoxy (—N(:O)=N—) compounds, hydrazine (—NHNH—) compounds or like intermediate compounds, and, all the intermediate compounds including hydroxylamino (—NHOH) compounds are subject to reduction into amino (—NH$_2$) compounds when reduced in the ordinary reduction process, so that it was difficult so far to obtain such hydroxylamino compounds stationarily at a high yield. It was reported by W. H. Beisler et al in Journal of American Chemical Society, 44, pp 2296 – 2306 (1922), that 1-hydroxylaminoanthraquinone was formed by treating 1-nitroanthraquinone with hydrogen sulfide in pyridine solution. This process seems to be fairly successful, but there is a difficulty in separation and purification of a reaction product because of deposition of solid sulfur by reduction of the reducing agent.

Hitherto, 1-aminoanthraquinone which is the most important among aminoanthraquinones has been produced industrially in the following two processes:

1. in which anthraquinone-α-sulfonic acid prepared by sulfonation of anthraquinone is aminated, and
2. in which 1-nitroanthraquinone prepared by nitration of anthraquinone is reduced.

These processes, however, have various shortcomings as mentioned below. Namely, the process (1) needs as a catalyst for the sulfonation of anthraquinone a mercury compound which is very difficult to be recovered from reaction mixtures and contaminates waste water and the product to bring about pollution of biological environment. And, in the process (2) it is very difficult to obtain a product of a high purity because of inevitable formation of dinitro compounds as by-products.

Accordingly, an object of the present invention is to provide a novel process for the preparation of 1-substituted anthraquinones from 5-nitro-1,4,4a, 9a-tetrahydroanthraquinones.

Another object of the present invention is to provide a process for the preparation of 1-hydroxylaminoanthraquinones from 5-nitro-1,4,4a, 9a-tetrahydroanthraquinones.

A still another object of the present invention is to provide a process for the preparation of 1-aminoanthraquinones from 5-nitro-1,4,4a, 9a-tetrahydroanthraquinones.

A further object of the present invention is to provide a process for the preparation of 1-aminoanthraquinones from 1-hydroxylaminoanthraquinones.

A still further object of the present invention is to provide a novel process for the preparation of 1-hydroxylaminoanthraquinones and new uses thereof.

In accordance with the present invention, 1-substituted anthraquinones represented by the following general formula I

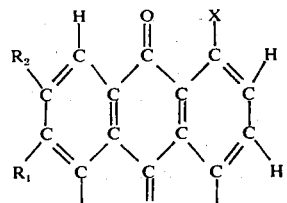

where, in the general formula, $R_1$ and $R_2$ represent individually a hydrogen atom or methyl group and x represents a hydroxylamino or amino group, are obtained by treating 5-nitro-1,4,4a, 9a-tetrahydroanthraquinones represented by the following general formula II

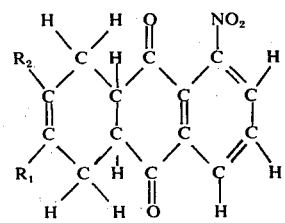

where, in the general formula, $R_1$ and $R_2$ represent individually a hydrogen atom or methyl group, in the presence of a basic compound in a liquid medium.

Compounds of the general formula II yield 1-hydroxylaminoanthraquinones when treated with a basic compound only, while they yield 1-aminoanthraquinones when treated with either a basic reducing agent or a combination of a basic compound and a reducing agent.

Thus, in accordance with the process of the present invention, by treating compounds of the general formula II with a basic compound in a liquid medium there may be obtained with ease 1-hydroxylaminoanthraquinones. The 1-hydroxylaminoanthraquinones thus obtained are used for the preparation of various compounds such as 1-aminoanthraquinones, and the 1-aminoanthraquinones thus obtained are of great value as intermediates for dyes.

Figure 2:
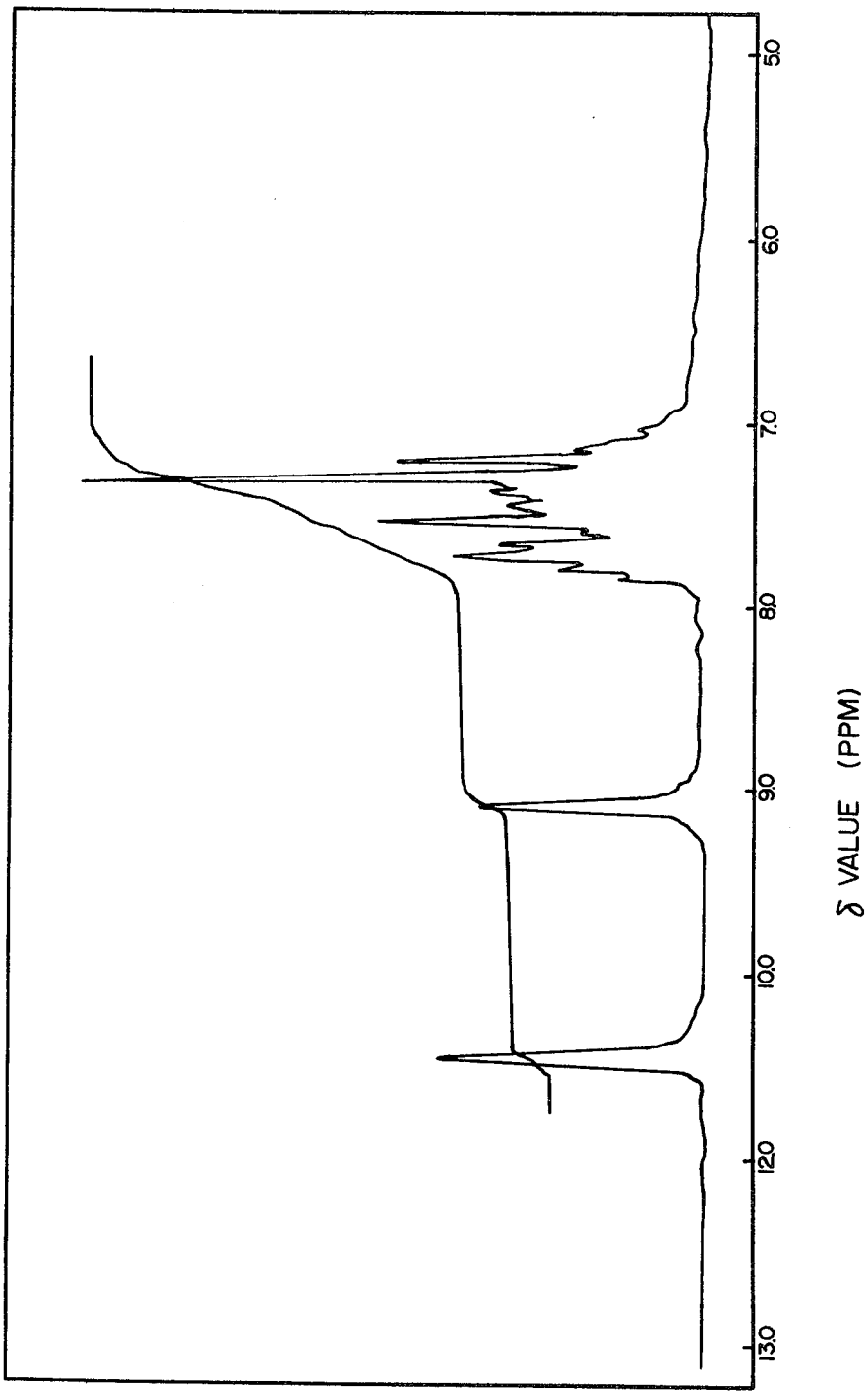

The present invention will be understood best in connection with the accompanying drawings wherein;

FIG. 1 shows an infrared absorption spectrum of crude 1-hydroxylaminoanthraquinone prepared in Example 1, and FIG. 2 shows a NMR spectrum of the crude 1-hydroxylaminoanthraquinone prepared in Example 1.

The 5-nitro-1,4,4a, 9a-tetrahydroanthraquinones as starting materials such compounds that may easily be obtained by adding butadienes to 5-nitro-1,4-naphthoquinone through Diels-Alder reaction, so that the process of the present invention is a very advantageous process in industrial point of view for the preparation of the 1-substituted anthraquinones of the general formula I. The 5-nitro-1,4-naphthoquinone may be prepared by, e.g., electrolytic oxidation of 1-nitronaphthalene or nitration of 1,4-naphthoquinone, and among processes of the latter type the process as disclosed in our application Ser. No. 493,607 now U.S. Pat. No. 3,941,815, provides the best result in the manufacture of 5-nitro-1,4-naphthoquinone. The representatives of the 5-nitro-1,4,4a, 9a-tetrahydroanthraquinones as starting materials include 5-nitro-1,4,4a, 9a- tetrahydroanthraquinone, 2- or 3-methyl-5-nitro-1,4,4a, 9a-tetrahydroanthraquinone and 2,3-dimethyl-5-nitro-1,4,4a, 9a-tetrahydroanthraquinone, among which 5-nitro-1,4,4a, 9a-tetrahydroanthraquinone is useful as a starting material for the preparation of the most important dye intermediate 1-hydroxylaminoanthraquinone or 1-aminoanthraquinone.

It is essential for the process of the present invention to carry out the reaction in the presence of a basic compound, though it is good enough to use the basic compound in an amount sufficient to maintain the rection mixture basic. The basic compound may be any of those compounds as generally be regarded as basic substance, such as, e.g.;

1. Oxides, hydroxides, sulfides and weak acid salts of Group Ia, Ib, IIa and IIb metals of the periodic table, such as magnesium oxide, calcium oxide, beryllium oxide, lithium hydroxide, sodium hydroxide, potassium hydroxide, rubidium hydroxide, cesium hydroxide, barium hydroxide, lithium bicarbonate, sodium bicarbonate, potassium bicarbonate, rubidium bicarbonate, lithium carbonate, sodium carbonate, potassium carbonate, sodium acetate, potassium acetate, sodium borate, potassium borate, sodium sulfite, potassium sulfite, sodium thiosulfate, potassium thiosulfate, tripotassium phosphate, trisodium phosphate, dipotassium phosphate, disodium phosphate, potassium permanganate, sodium chromate, sodium sulfide, potassium sulfide, sodium phenolate, potassium phenolate, sodium benzoate, potassium tartarate and tetrasodium ethylenediaminetetraacetate, 2. ammonia and ammonium carbonate, 3. alcoholates of Group Ia and IIa metals of the periodic table, such as lithium methylate, sodium methylate, potassium methylate, sodium ethylate, potassium ethylate, magnesium ethylate, calcium ethylate, sodium isopropylate, potassium isopropylate, calcium isopropylate, magnesium isopropylate, sodium butoxide, potassium butoxide and the like, and 4. primary amines, secondary amines, tertiary amines, quaternary ammonium hydroxides and like nitrogen-containing basic compounds, such as monomethylamine, dimethylamine, trimethylamine, monoethylamine, diethylamine, triethylamine, mono-n-propylamine, di-n-propylamine, tri-n-propylamine, monoisopropylamine, diisopropylamine, n-butylamines, isobutylamines, sec-butylamines, tert-butylamines, pentylamines, hexylamines, heptylamines, octylamines, cyclohexylamines, ethanolamine diethanolamine, triethanolamine, isopropanolamine, diisopropanolamine, triisopropanolamine, aniline, benzyldimethylamine, triphenylamine, benzylamine, ethylenediamine, 1,2-propylenediamine, 1,3-propylenediamine, diethylenetriamine, triethylenetetramine, ethyleneimine, propyleneimine, piperazine, morphorine, pyridine, pyrazine, pyrimidine, pyrazole, 1,8-diazabicyclo(5,4,0)undecene-7, tetramethylammonium hydroxide, tetraethylammonium hydroxide, tetra-n-propylammonium hydroxide, tetra-n-butylammonium hydroxide, benzyl trimethylammonium hydroxide, phenyl triethylammonium hydroxide, dimethyldiethylammonium hydroxide, urea, thiourea, methyl and ethyl esters of glycine and the like.

In the process of the present invention suitably used are hydroxides, carbonates, bicarbonates, sulfides, phosphates and thiosulfates of alkali metals, calcium hydroxide, barium hydroxide and ammonia, alkylamines, urea, pyridine and quaternary ammonium hydroxides. The basic compound may be used in amounts of at least 0.01, preferably 0.1 – 100 parts by weight per 100 parts by weight of the compound of the general formula II as a starting material. In a case of using a strong base such as sodium hydroxide, sodium sulfide, sodium phenolate, sodium alkoxides and quaternary ammonium hydroxides, it is preferred to be used in an amount of 0.01 to 1.0 parts by weight of 100 parts by weight of the compound of the general formula II, but in case of weak basic non-reducing compound such as liquid amines, sodium acetate, disodium phosphate and sodium bicarbonate, it may be used in an amount of 1 to 100 parts by weight of 100 parts of the compound of the general formula II.

In the process of the present invention, it is preferable to use a basic compound not effecting reductivity to the product to obtain a 1-hydroxylaminoanthraquinone as a main product.

In the process of the present invention in which reaction is carried out in liquid phase, there may be used as liquid medium any liquid which is relatively stable in oxidative or reductive atmosphere. Examples of the liquid media suitably used are: water; methanol, ethanol, isopropanol, butanols and like alcohols; ethyleneglycol monomethyl ether (methyl-Cellosolve), ethyleneglycol monobutyl ether and like glycol ethers; ethyleneglycol, diethyleneglycol, propyleneglycol and like glycols; benzene, toluene, xylene and like aromatic hydrocarbons; and ligroin, acetone, methyl ethyl ketone, tetrahydrofurane, dimethylformamide, dimethylsulfoxide, pyridine, ethanolamines and like solvents, and mixtures thereof.

In the process of the present invention, it is unnecessary to completely dissolve the 5-nitro-1,4,4a, 9a-tetrahydroanthraquinone as starting material in such a liquid medium as mentioned above, and the reaction advances also in suspension. For attaining efficient separation of the product, 1-hydroxylaminoanthraquinones, it is preferred to reduce the solubility of the 1-hydroxylaminoanthraquinones in the liquid medium. This is attained by use of a mixed solvent containing water, ligroin or like poor solvent or by adding such a poor solvent to the reaction mixture after reaction to reduce the solubility in the liquid medium. For instance, 1-hydroxylaminoanthraquinone is easily soluble in dimethylsulfoxide and soluble in acetone and ethanol but insoluble in water and ligroin. Similarly, in the preparation of 1-aminoanthraquinones, it is preferred to select a liquid medium from which the product is easily separable.

In the preparation of 1-aminoanthraquinones, there may be used as the reducing agent any compound which has been known to have a reducing power of reducing nitro compound into amino compound. Representative examples of the reducing agents are, for examples, hydrogen sulfide; hydrosulfides, such as lithium hydrosulfide, sodium hydrosulfide, potassium hydrosulfide, rubidium hydrosulfide and ammonium hydrosulfide; sulfides, such as lithium sulfide, sodium sulfide, potassium sulfide, cesium sulfide and ammonium sulfide; disulfides and polysulfides, such as sodium disulfide, sodium polysulfide, potassium disulfide, potassium polysulfide, ammonium disulfide and ammonium polysulfides; and like sulfur-containing compound and, in addition thereto, elementary sulfur, ammonia, metallic zinc, metallic iron, metallic aluminum, metallic magnesium, metallic nickel, catalytically activated hydrogen, sugars such as glucose, fructose, sucrose and maltose, paraformaldehyde, oxalic acid and its salts, formic acid and its salts, ascorbic acid and its salts, and the like.

In the practice of the process of the present invention in commercial scale, there may advantageously be used as the reducing agents hydrogen sulfide, ammonium sulfide, sodium sulfide, sodium disulfide, elementary sulfur and metallic zinc. It is preferred to use the reducing agent in excess over the amount necessary for completion of reduction of the starting material 5-nitro-1,4,4a, 9a-tetrahydroanthraquinones, optimally in amount of 2 to 6 oxidation-reduction equivalents per mole of the starting material, and after reaction the excess of the reducing agent may be recovered for recirculation.

The reaction temperature ranges from 0° to 200°C, preferably from 30° to 150°C and optimally from 50° to 110°C. The reaction time ranges from 20 to 120 minutes in the preparation of 1-hydroxylaminoanthraquinones and, on the other hand, from 1 to 20 hours in the preparation of 1-aminoanthraquinones.

Thus, 1-hydroxylaminoanthraquinones or 1-aminoanthraquinones are obtained steadily at a quantitative high yield.

According to our observation, 1-hydroxylaminoanthraquinone purified by means of methanol exhibited no distinct melting point and decomposed at 200° to 240°C.

The 1-hydroxylaminoanthraquinones thus obtained are further reduced to obtain 1-aminoanthraquinones in the following processes:

1. a process in which 1-hydroxylaminoanthraquinones are reduced by means of at least one metal selected from the group consisting of iron, nickel, zinc, magnesium and aluminum and a mineral acid in the presence of an aliphatic monohydric alcohol containing 1 to 4 carbon atoms, 2. a process in which 1-hydroxylaminoanthraquinones are reduced by means of at least one metal selected from the group consisting of iron, nickel, zinc, magnesium and aluminum and a mineral acid in the presence of ethyleneglycol monoalkyl ethers, or 3. a process in which 1-hydroxylaminoanthraquinones are catalytically reduced with hydrogen in the presence of ethyleneglycol monoalkyl ethers.

The reducing agent used in the process of the present invention is at least one metal selected from the group consisting of iron, nickel, zinc, magnesium and aluminum. The metal should be supplied as it is to a reaction system, though its form does not matter. However, it is preferred to use the metal in the form of powder or ribbon from the industrial aspect, and as the metal preferred are iron, zinc and aluminum because of their low prices. The metals as reducing agent are used in amounts of 2 to 6 oxidation-reduction equivalents per mole of 1-hydroxylaminoanthraquinones.

The mineral acid used in the process of the present invention includes hydrochloric acid, sulfuric acid, phosphoric acid and the like, though preferred are hydrochloric acid and sulfuric acid, and the mineral acid is used in amounts sufficient to form salt with such a metal consumed in the aforesaid reduction reaction or more.

The aliphatic monohydric alcohol used as the reaction medium is of a carbon atom number of 1 to 4, such as, e.g., methanol, ethanol, n-propanol, isopropanol, n-butanol, isobutanol, sec-butanol and tert-butanol, and mixtures thereof. By the presence of the aforesaid lower alcohol in the reaction system portion of the starting material 1-hydroxylaminoanthraquinones is solubilized and thereby a smooth progress of reaction is promoted. And, it has been found that incorporation of water in the alcohol as reaction medium makes it easy to process the reaction mixture after reaction. That is to say, the presence of a small amount of water in the reaction system lowers the solubility of the reaction product 1-aminoanthraquinones to increase the recovery of the product in the form of crystals, reduces formation of higher-order reduction products, such as anthrones, by overprogress of reduction caused by use of somewhat excess metal and dissolves the metal salt formed to facilitate, e.g., stirring. These effects are obtained especially when the weight ratio of alcohol to (alcohol + water) is at least 0.2, preferably at least 0.5. It has been found that when the weight ratio is less than 0.2 the reaction rate is low and crystals of 1-aminoanthraquinones formed are too fine to be recovered by filtration.

It is good enough for the reaction medium to be used in an amount as to form a stirrable reaction mixture, though the reaction medium preferably is used in an amount of at least 4 times the weight of 1-hydroxylaminoanthraquinones, more desirably 10 to 50 times the weight of 1-hydroxylaminoanthraquinone, in the practice of the process of the present invention.

The ethyleneglycol monoalkyl ethers used as the other reaction medium includes ethyleneglycol monoalkylethers and diethyleneglycol monoalkyl ethers represented by the general formula III

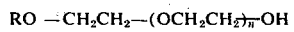     (III)

where, in the formula, R represents an alkyl group containing 1 to 8 carbon atoms, preferably 1 to 4 carbon atoms, and $n$ represents an integer of 0 or 1. Representative examples are, e.g., mono- or diethyleneglycol monomethyl ether, -monoethyl ether, -mono-n-propyl ether, -mono-isopropyl ether, -mono-n-butyl ether, -monoisobutyl ether, -mono-sec-butyl ether, -mono-tert-butyl ether, -monopentyl ether, -mono-hexyl ether and -monooctyl ether. The presence of such ethyleneglycol monoalkyl ethers in the reaction system solubilizes portion of the starting material 1-hydroxylaminoanthraquinones.

Hitherto, synthesis of aromatic amines has usually been made by reducing aromatic nitro compounds by means of iron and a mineral acid. However, in case of 1-hydroxylaminoanthraquinones as the starting material in the process of the present invention, the reaction rate is very low when reduced in the conventional manner by means of a metal and a mineral acid and the most part of metal is consumed for generation of gaseous hydrogen, so that this method seems to be unpracticable for the commercial production of 1-aminoanthraquinones. Therefore, the effect of use of the aforesaid liquid medium has to be said remarkable. In addition, use of water in combination with such a liquid medium is very effective for the performance of the process of the present invention, especially in an amount as to provide in the reaction system a weight ratio of ethyleneglycol monoalkyl ether to (water + ethyleneglycol monoalkyl ether) of at least 0.2, preferably of at least 0.5. When the aforesaid weight ratio is less than 0.2, the reaction rate of reduction is too low and crystals of the 1-aminoanthraquinones formed are too fine to be recovered by filteration. The presence of water (including water contained in a mineral acid used) in the reaction system exerts effects of reducing the solubility of 1-aminoanthraquinones and of increasing the yield of crystals and, in addition, of preventing formaton of higher-order reduction products, such as anthrones, by the action of somewhat excess metal, of dissolving a metal salt formed and of facilitating stirring of the reaction mixture. It is good enough for the liquid medium to be used in an amount as to form a stirrable reaction mixture, though the reaction medium preferably is used in an amount of at least 4, more desirably of 10 to 50 times the weight of 1-hydroxylaminoanthraquinones.

As the catalyst to be used for the catalytic reduction by hydrogen there may be used any of the known catalysts generally regarded as hydrogenation catalysts, such as nickel, cobalt, iron, copper, platinum or palladium. The catalyst may be used in amounts of 0.1 to 30, preferably of 1 to 10% by weight based on the weight of 1-hydroxylaminoanthraquinones. The 1-aminoanthraquinones formed may be separated from the reaction mixture in a conventional manner and may be obtained in a yield of 80% or more of theoretical yield.

The reduction of 1-hydroxylaminoanthraquinones is conducted at temperatures of 0° to 200°C. The reduction by means of at least one metal selected from the group consisting of iron, nickel, zinc, magnesium and aluminum and a mineral acid in the presence of an aliphatic monohydric alcohol or (di)ethyleneglycol monoalkyl ether is conducted at temperatures of 50° to 150°, preferably of 60° to 110°C. On the other hand, the catalytic reduction by hydrogen preferably is conducted at temperatures of 20° to 150°C, and more desirably of 50° to 150°C. The reaction time varies depending on the reaction temperature, the amounts of metal and mineral acid or of reducing catalyst used and the nature and concentration of reaction medium, though sufficient is a time of 1 to 20 hours.

The catalytic reduction by hydrogen is carried out by suspending 1-hydroxylaminoanthraquinone and a hydroganation catalyst in the reaction medium as mentioned above and then introducing gaseous hydrogen into the suspension under normal pressure or under pressure. In this case, the aforesaid reaction medium is used in an amount as to form a stirrable slurry of the starting material and the catalyst, i.e. in an amount of at least 4, preferably of 10 to 50 times the weight of 1-hydroxylaminoanthraquinones.

In the following Examples, all parts and percentages are by weight unless otherwise designated.

EXAMPLES 1 to 4

A mixture of 5 parts of 5-nitro-1,4,4a,9a-tetrahydroanthraquinone, 70 parts of methanol and a basic compound, as listed in the following Table 1 in an amount as indicated therein, was stirred at 60°C for 1 hour, then cooled to 20°C and crystals formed were filtered, washed with water and dried under reduced pressure. The mother liquor was distilled to remove methanol and then washed with water to remove the basic compound and recover crystals. The crystals thus obtained were confirmed to be of 1-hydroxylaminoanthraquinone by infrared absorption spectrum, elementary analysis, NMR spectrum and determination of reduction equivalent. The yields were as summarized in the Table 1.

Table 1

| Example Nos. | Basic compound Kinds | Amounts added (parts) | Yield of hydroxyl-aminoanthraquinone (parts) | 1-Hydroxylamino-anthraquinone remaining in mother liquor (parts) |
|---|---|---|---|---|
| 1 | KOH | 0.06 | 4.25 | 0.35 |
| 2 | $NH_3$ | 0.5 | 4.30 | 0.35 |
| 3 | $(C_2H_5)_4NOH$ | 0.1 | 4.30 | 0.25 |
| 4 | $Ca(OH)_2$ | 0.1 | 4.26 | 0.35 |

The above results indicate that the yields are almost quantitative.

In FIG. 1 there is shown an infrared absorption spectrum determined on a crude 1-hydroxylaminoanthraquinone obtained in Example 1 and in FIG. 2 is shown a NMR spectrum determined on the crude 1-hydroxylaminoanthraquinone obtained in Example 1 in dimethylsulfoxide solution at 60MHz. And, in the following Table 2 were summarized the results of elementary analysis in comparison with the calculated values, on crude 1-hydroxylaminoanthraquinone obtained in Example 1 and in Example 2.

Table 2

| | Values of elementary analysis (%) | | |
|---|---|---|---|
| | Carbon | Hydrogen | Nitrogen |
| Example 1 (found) | 70.10 | 3.83 | 5.82 |
| Example 2 (found) | 70.15 | 3.80 | 5.83 |
| $C_{14}H_9O_3N$ (calculated) | 70.29 | 3.79 | 5.86 |

EXAMPLES 5 – 12

A mixture of 5.0 parts of 5-nitro-1,4,4a,9a-tetrahydroanthraquinone with a solvent and a basic compound, of kinds and in amounts as listed in the following Table 3, was stirred for 1 hour at a temperature, as indicated in the Table 3, then cooled to 20°c, filtered to recover crystals and dried under reduced pressure to obtain the results as shown in the Table 3.

The product in each Example was confirmed to be 1-hydroxylaminoanthraquinone by determination of infrared absorption spectrum, and it was confirmed that in filtrates in Examples 5 to 12 there were contained little amounts of 1-hydroxylaminoanthraquinone.

Table 3

| Example Nos. | Solvent Kinds | Amounts (parts) | Basic compound Kinds | Amounts (parts) | Reaction temp. (°C) | Yields of 1-hydroxyl-aminoanthra-quinone (parts) |
|---|---|---|---|---|---|---|
| 5 | Methylcellosolve | 50 | $Na_2CO_3$ | 0.04 | 90 | 4.35 |
|   | Water | 50 | | | | |
| 6 | Acetone | 40 | $Na_3PO_4$ | 0.05 | 50 | 4.25 |
|   | Water | 50 | | | | |
| 7 | n-Butanol | 80 | $HOCH_2CH_2NH_2$ | 0.50 | 60 | 4.30 |
| 8 | Methylcellosolve | 50 | $CH_3COONa$ | 0.10 | 100 | 4.30 |
|   | Water | 50 | | | | |
| 9 | Tetrahydrofuran | 40 | $Na_2S$ | 0.05 | 60 | 4.33 |
|   | Water | 50 | | | | |
| 10 | Methylcellosolve | 50 | $(NH_2)_2CO$ | 1.00 | 70 | 4.35 |
|   | Water | 50 | | | | |
| 11 | Methylcellosolve | 50 | $Na_2S_2O_3$ | 0.50 | 70 | 4.34 |
|   | Water | 50 | | | | |
| 12 | Ligroin | 80 | $(n-C_4H_9)_2NH$ | 1.0 | 70 | 4.36 |

EXAMPLE 13

A mixture of 5.0 parts of 5-nitro-1,4,4a,9a-tetrahydroanthraquinone with 80 parts of toluene and 1.0 part of n-butylamine was stirred at 70°C for 2 hours. The mixture was then distilled under a reduced pressure of 100 mm Hg to remove toluene, washed with 50 parts of methanol and dried under reduced pressure to obtain 4.4 parts of 1-hydroxylaminoanthraquinone.

EXAMPLE 14

A mixture of 5.0 parts of 5-nitro-1,4,4a,9a-tetrahydroanthraquinone with 50 parts of pyridine was stirred at 70°C for 1 hour and then poured into 500 parts of water to precipitate crystals. After cooled to 20°C, the crystals were recovered by filtration, washed with water and dried under reduced pressure to obtain 4.5 parts of 1-hydroxylaminoanthraquinone.

EXAMPLE 15

A mixture of 5.0 parts of 5-nitro-2,3-dimethyl-1,4,4a,9a-tetrahydroanthraquinone with 50 parts of water, 50 parts of methylcellosolve and 0.05 parts of potassium carbonate was stirred at 60°C for 1 hour, then cooled to 20°C and filtered to recover crystals. The crystals were washed with water and dried under reduced pressure to obtain 4.5 parts of 5-hydroxylamino-2,3-dimethylanthraquinone.

Elementary analysis Found: C, 71.85%; H, 4.92%; N, 5.22%. $C_{16}H_{12}O_2N$: Calculated: C, 71.89%; H, 4.90%; N, 5.24%.

EXAMPLE 16

A mixture of 5.0 parts of 5-nitro-1,4,4a,9a-tetrahydroanthraquinone with 100 parts of water and 5.0 parts of sodium sulfide enneahydrate was heated to 90°C with stirring, maintained at 90° to 100°C for 1 hour and cooled to 50°C. The reaction mixture was filtered and washed with water and the crystals thus obtained was dried at 80°C to obtain 4.3 parts of red crystals having a melting point of 252°C. The product was confirmed to be 1-aminoanthraquinone by infrared absorption spectrum.

EXAMPLES 17 to 20

Mixtures of each 5.0 parts of 5-nitro-1,4,4a,9a-tetrahydroanthraquinone with 30 parts of water, 70 parts of methylcellosolve and reducing agents and basic compounds, of kinds and in amounts as indicated in the following Table 4, were stirred at 90°–100°C for times, as indicated in the Table 4, then cooled to 40°C and filtered to recover crystals. The crystals were washed with water and dried under reduced pressure. In all of these Examples, the products were confirmed by infrared absorption spectrum to be 1-aminoanthraquinone. The yields of 1-aminoanthraquinone obtained in the form of crystals were as shown in the Table 4.

Table 4

| Example Nos. | Reducing agent Kinds | Amounts (parts) | Basic compound Kinds | Amounts (parts) | Reaction time (hours) | Yield of 1-amino-anthraquinone (pts) |
| --- | --- | --- | --- | --- | --- | --- |
| 17 | Hydrogen sulfide | 1 | Ammonia | 1 | 2 | 4.3 |
| 18 | Formic acid | 2 | Sodium hydroxide | 2 | 5 | 4.0 |
| 19 | Oxalic acid | 3 | Sodium hydroxide | 2 | 5 | 4.0 |
| 20 | Sucrose | 5 | Potassium hydroxide | 2 | 10 | 3.9 |

EXAMPLE 21

A mixture of 5.0 parts of 5-nitro-1,4,4a,9a-tetrahydroanthraquinone with 3 parts of zinc dust, 10 parts of a 20 wt % aqueous sodium hydroxide and 50 parts of ethanol was refluxed for 2 hours with stirring and, after cooled to 20°C, filtered. The residue was washed with water and poured into a dilute hydrochloric acid to dissolve zinc dust. Crystals were recovered by filration, washed with water and dried under reduced pressure to obtain 3.8 parts of 1-aminoanthraquinone.

EXAMPLE 22

A mixture of 5.0 parts of 5-nitro-1,4,4a,9a-tetrahydroanthraquinone with 100 parts of water, 2 parts of sulfur and 2 parts of calcium hydroxide was stirred at 95°C for 3 hours and then cooled to 25°C. Crystals precipitated were recovered by filteration, washed with water, then washed with a dilute hydrochloric acid to dissolving away calcium hydroxide and dried under reduced pressure to obtain 3.7 parts of crystalline 1-aminoanthraquinone.

EXAMPLE 23

A mixture of 5.0 parts of 5-nitro-1,4,4a,9a-tetrahydroanthraquinone with 50 parts of pyridine was stirred at 90°C for 2 hours with introducing thereinto 0.8 parts/hour of gaseous hydrogen sulfide. The reaction mixture was then cooled to 25°C and added with 50 parts of water to precipitate crystals. The crystals were recovered by filtration, washed with water and dried under reduced pressure to obtain 3.9 parts of 1-aminoanthraquinone.

EXAMPLE 24

To 5.0 parts of 5-nitro-2,3-dimethyl-1,4,4a,9a-tetrahydroanthraquinone there was added 100 parts of water and then, with stirring at 90°C, 20 parts of a 10 wt % aqueous sodium sulfide. The reaction mixture thus formed was maintained at 90° – 95°C for 1 hour and, after cooled to 25°C, filtered to recover crystals. The crystals were washed with water and dried under reduced pressure to obtain 4.5 parts of 5-amino-2,3-dimethylanthraquinone of a melting point of 222°C.

EXAMPLE 25

1-Hydroxylaminoanthraquinone 50 parts was stirred into a mixture of methyl alcohol 700 parts, water 100 parts and a 35% aqueous hydrochloric acid 60 parts. The reaction mixture was heated to 70°C and then added with zinc dust 16 parts little by little over 1 hour. After the reaction at 70°C for 3 hours, the reaction mixture was cooled to 25°C, filtered, washed with water and dried to obtain 42.5 parts of crystalline 1-aminoanthraquinone of a purity of 93%.

EXAMPLE 26

To a mixture of 600 parts of methyl alcohol, 200 parts of water and 70 parts of a 35% aqueous hydrochloric acid there was added with stirring 50 parts of 1-hydroxylaminoanthraquinone and the resulting mixture was heated to 70°C. After addition of 17 parts of metallic iron in the form of ribbon little by little over 1 hour, the reaction mixture was maintained at 70°C for additional 4 hours, then cooled to 25°C and filtered. The residue was washed with water, then dissolved in 500 parts of dimethylformamide and filtered to remove residual metallic iron. Dimethylformamide in the filtrate was removed by distillation under reduced pressure to obtain 42.0 parts of 1-aminoanthraquinone of a purity of 92%.

EXAMPLES 27 to 31

To a mixture of an alcohol, water and an acid, of kinds and in amounts as listed in the following Table 5, there was added 50 parts of 1-hydroxylaminoanthraquinone. The reaction mixture was, after heated to a temperature as indicated in the Table 5, added with zinc dust or iron ribbon little by little over 1 hour and then maintained at the reaction temperature for a time as indicated in the Table 5. The reaction mixture was then cooled to 25°C and processed thereafter in the similar manner as in Example 26 to recover 1-aminoanthraquinone in the yields as summarized in the Table 5.

It was confirmed, as shown in the Table 5, that the solubility of aminoanthraquinone in the reaction medium increased as the concentration of alcohol therein increased and a portion of aminoanthraquinone formed passed into the filtrate.

Table 5

| Example Nos. | Solvent and acid Kinds | (parts) | (alcohol)/(alcohol + water) ratio in reaction system |
| --- | --- | --- | --- |
| 27 | Methyl alcohol | 500 | |
| | Water | 400 | 0.53 |
| | 35 % HCl | 60 | |
| 28 | Ethyl alcohol | 400 | |
| | Water | 100 | 0.80 |
| | $H_2SO_4$ | 30 | |
| 29 | Isopropyl alcohol | 800 | |
| | Water | 100 | 0.89 |

Table 5-continued

|    |                 |     |      |
|----|-----------------|-----|------|
|    | H₂SO₄           | 30  |      |
| 30 | Sec-butyl alcohol | 800 | 0.95 |
|    | 35 % HCl        | 60  |      |
| 31 | Methyl alcohol  | 800 | 1.00 |
|    | H₂SO₄           | 30  |      |

| Reducing agent | (parts) | Reaction temperature (°C) | and time (hours) | Yield (parts) | and Purity (%) |
|---|---|---|---|---|---|
| Iron ribbon | 17 | 77 | 6 | 43.6 | 91 |
| Iron ribbon | 17 | 80 | 4 | 41.5 | 94 |
| Iron ribbon | 17 | 65 | 6 | 38.5 | 95 |
| Zinc dust | 16 | 75 | 3 | 41.0 | 94 |
| Zinc dust | 16 | 65 | 4 | 37.5 | 96 |

EXAMPLE 32

50 Parts of 2,3-dimethyl-5-hydroxylaminoanthraquinone was added to a mixture of 600 parts of methyl alcohol, 200 parts of water and 60 parts of a 35 % aqueous hydrochloric acid and the mixture was heated with stirring to 70°C, then added thereto 15 parts of zinc dust little by little over 1 hour. The reaction mixture was maintained at 70°C for additional 3 hours and then cooled to 25°C and filtered. The residue was washed with water and dried to obtain 42.8 parts of 2,3-dimethyl-5-aminoanthraquinone of a purity of 95 %.

COMPARATIVE EXAMPLE

To 700 parts of a 3 % aqueous hydrochloric acid there was added 50 parts of 1-hydroxylaminoanthraquinone and the mixture was heated with stirring to 70°C, then added thereto little by little 16 parts of zinc dust over 1 hour. The reaction mixture was maintained at 70°C for additional 4 hours. Zinc dust was completely consumed during the reaction course but a fairly large amount of 1-hydroxylaminoanthraquinone remained unreacted. The reaction mixture was cooled to 25°C and filtered. The residue was washed with water and then with 200 parts of a 3 % solution of sodium hydroxide in a 20 % aqueous acetone to extract therefrom unreacted 1-hydroxylaminoanthraquinone and washed with water again and dried to obtain 15.5 parts of 1-aminoanthraquinone of a purity of 90 %.

EXAMPLE 33

50 Parts of 1-hydroxylaminoanthraquinone was stirred into a mixture of 700 parts of diethyleneglycol monomethyl ether, 100 parts of water and 30 parts of conc. sulfuric acid, then added thereto little by little 16 parts of zinc dust over 1 hour after heating to 80°C. The reaction mixture was maintained at 80°C for additional 2 hours and then filtered. The filtrate was washed with water and dried to obtain 43.5 parts of 1-aminoanthraquinone of a purity of 94 %.

EXAMPLE 34

50 Parts of 1-hydroxylaminoanthraquinone was stirred into a mixture of 500 parts of ethyleneglycol monobutyl ether, 200 parts of water and 60 parts of a 35 % aqueous hydrochloric acid. After heated to 75°C, the mixture was added with 17 parts of iron ribbon little by little over 1 hour and maintained at 75°C for additional 3 hours. After cooled to 25°C, the reaction mixture was filtered and the residue was washed with water and extracted with 500 parts of dimethylformamide to separate the resulting 1-aminoanthraquinone from unreacted metal. The extract was distilled for removal of dimethylformamide to obtain 42.5 parts of 1-aminoanthraquinone of a purity of 93 %.

EXAMPLE 35

50 Parts of 1-hydroxylaminoanthraquinone was stirred into a mixture of 1,000 parts of ethyleneglycol monomethyl ether and 30 parts of conc. sulfuric acid. After heated to 75°C, the mixture was added with 17 parts of iron dust little by little over 1 hour and maintained at 75°C for additional 3 hours. The reaction mixture was then filtered while hot and the residue was washed with 100 parts of ethyleneglycol monomethyl ether heated at 80°C. Thus, unreacted metallic iron and iron sulfate were separated as residue. The filtrate was added with 200 parts of water and then cooled to 25°C to precipitate crystals. The crystals were recovered by filtration, washed with water and dried to obtain 43.5 parts of 1-aminoanthraquinone of a purity of 95 %.

EXAMPLE 36

50 Parts of 2,3-dimethyl-5-hydroxylaminoanthraquinone was stirred into a mixture of 700 parts of ethyleneglycol monomethyl ether, 200 parts of water and 60 parts of a 35 % aqueous hydrochloric acid, and the mixture was then heated to 75°C. To the mixture there was added little by little 16 parts of zinc dust over 1 hour. The reaction mixture was maintained at 75°C for additional 3 hours, then cooled to 25°C and filtered. The residue was washed with water and dried to obtain 43.6 parts of 2,3-dimethyl-5-aminoanthraquinone of a purity of 95 %.

EXAMPLE 37

To 100 parts of ethyleneglycol monomethyl ether (so called methyl-Cellosolve) there were added 5.0 parts of 1-hydroxylaminoanthraquinone and 0.25 part of Raney nickel. The reaction mixture was heated to 80°C over 30 minutes and maintained at 80°C for 4 hours, with stirring, while introducing thereinto 0.04 parts/hour of gaseous hydrogen. The reaction mixture was then purged of gaseous hydrogen with gaseous nitrogen, heated to 100°C and filtered while hot to separate the catalyst as residue. The filtrate was, while maintained at 80°C, added with 100 parts of water, with stirring, to precipitate crystals. The slurry thus formed was then cooled to room temperature and filtered. The residue was washed with 5 parts of methanol and dried to obtain 4.2 parts of 1-aminoanthraquinone of a purity of 97 %. In the filtrate there remained 0.1 part of 1-aminoanthraquinone dissolved.

EXAMPLES 38 to 41

To a reaction medium, as shown in the following Table 6, there were added 5.0 parts of 1-hydroxylaminoanthraquinone and a catalyst of a kind and in an amount, as indicated in the Table 6. The reaction mixture thus formed was stirred under the reaction conditions as indicated in the Table 6. In Example 40 and 41, there was introduced gaseous hydrogen into reaction mixtures.

The reaction mixture was, after reaction step, processed in the similar manner as in Example 37. In all of these Examples, there remained little 1-aminoanthraquinone in filtrates.

Table 6

| Example Nos. | Reaction medium Kinds | (parts) | Catalyst (parts) | Gaseous hydrogen (parts/hr) | (gauge atm.) |
|---|---|---|---|---|---|
| 38 | Ethylene glycol monobutyl ether | 90 | Raney nickel 0.25 | 0.04 | 0 |
|  | Water | 10 |  |  |  |
| 39 | Diethylene glycol monoethyl ether | 100 | Raney nickel 0.25 | 0.04 | 0 |
| 40 | Ethylene glycol monomethyl ether | 100 | 5 % Pd supporting activated carbon 2 | — | 0.2 |
| 41 | Ethylene glycol monoethyl ether | 100 | Raney nickel 0.05 | — | 40 |

| Temperature (°C) | Time (hrs) | 1-Aminoanthraquinone Yield (parts) | Purity (%) |
|---|---|---|---|
| 125 | 5 | 4.3 | 96 |
| 100 | 6 | 4.1 | 97 |
| 80 | 7 | 4.3 | 96 |
| 80 | 20 | 4.4 | 95 |

EXAMPLE 42

The same procedure as in Example 37 was repeated except that there was used 5.0 parts of 2,3-dimethyl-5-hydroxylaminoanthraquinone, to obtain 4.3 parts of 2,3-dimethyl-5-aminoanthraquinone of a purity of 97 %.

What is claimed is:

1. A process for the preparation of a 1-substituted anthraquinone having the general formula (I)

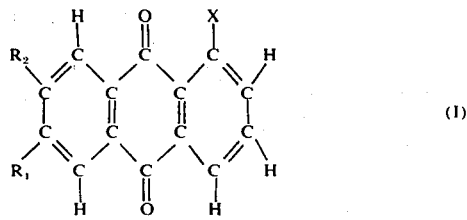

(I)

where, in the formula, $R_1$ and $R_2$ individually represent a hydrogen atom or methyl group and X represents a hydroxylamino or amino group,
which comprises treating a 5-nitro-1,4,4a,9a -tetrahydroanthraquinone having the general formula (II)

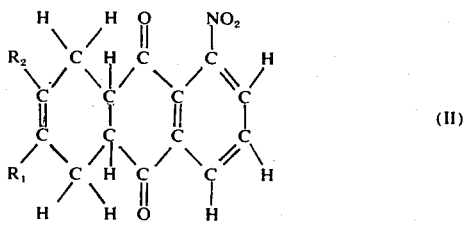

(II)

where, in the formula, $R_1$ and $R_2$ individually represent a hydrogen atom or methyl group
in the presence of a basic compound in a liquid medium whereby during the course of the reaction the ring structure is oxidized and the nitro group is partially or completely reduced to provide a product consisting essentially of the 1-substituted anthraquinone of the above general formula (I).

2. A process of claim 1 in which the basic compound is at least one member selected from the group consisting of oxides, hydroxides, weak acid salts and alcoholates of the group I and II metals of the periodic table, ammonia, ammonium carbonate, primary amines, secondary amines, tertiary amines, quaternary ammonium hydroxides and urea.

3. A process of claim 1 in which the basic compound is at least one member selected from the group consisting of hydroxides, carbonates, bicarbonates, sulfides, acetates, phosphates and thiosulfates of alkali metals, ammonia, alkylamines, urea, pyridine and quaternary ammonium hydroxides.

4. A process of claim 1 in which the basic compound is used in an amount of at least 0.01 parts by weight per 100 parts by weight of the compound represented by the general formula II.

5. A process of claim 1 in which the basic compound is used in an amount of 0.1 to 100 parts by weight per 100 parts by weight of the compound represented by the general formula II.

6. A process of claim 1 in which the basic compound is a liquid amine compound and used in a solvent amount.

7. A process of claim 1 in which the treatment is carried out at a temperature of 0° to 200°C.

8. A process of claim 1 in which the treatment is carried out at a temperature of 30° to 150°C.

9. A process of claim 1 in which the compound having the general formula II is 5-nitro-1,4,4a, 9a-tetrahydroanthraquinone.

10. A process of claim 1 in which the 1-substituted anthraquinone having the general formula I is 1-hydroxylaminoanthraquinone.

11. A process of claim 1 in which the 1-substituted anthraquinone having the general formula I is 1-aminoanthraquinone.

12. The process of claim 1 wherein the liquid medium is a liquid that is stable in an oxidative or reductive environment. pg,35

13. A process for the preparation of 1-hydroxylaminoanthraquinones comprising treating at a temperature of 0° to 200°C in a liquid medium a 5-nitro-1,4,4a, 9a-tetrahydroanthraquinone having the general formula (II) with at least 0.01 parts by weight, per 100 parts by weight of said anthraquinone, of a basic compound whereby during the course of the reaction the ring structure is oxidized and the nitro group is partially reduced to provide a product consisting essentially of a 1-hydroxylaminoanthraquinone.

14. A process for the preparation of 1-hydroxylaminoanthraquinones comprising treating at a temperature of 30° to 150°C in a liquid medium a 5-nitro-1,4, 4a, 9a-tetrahydroanthraquinone having the general formula (II) with 0.01 to 100 parts by weight, per 100 parts by weight of said anthraquinone, of a basic non-reducing compound whereby during the course of the reaction the ring structure is oxidized and the nitro group is partially reduced to provide a product consisting essentially of a 1-hydroxylaminoanthraquinone.

15. A process for the preparation of 1-hydroxylaminoanthraquinones comprising treating at a temperature of 30° to 150°C in a liquid medium a 5-nitro-1,4, 4a, 9a-tetrahydroanthraquinone having the general formula (II) with 0.01 to 1 part by weight, per 100 parts by weight of said anthraquinone, of a strong basic compound whereby during the course of the reaction the ring structure is oxidized and the nitro group is partially reduced to provide a product consisting essentially of a 1-hydroxylaminoanthraquinone.

16. A process for the preparation of 1-hydroxylaminoanthraquinone comprising treating at a temperature of 30° to 150°C in a liquid medium a 5-nitro-1,4,4a, 9a-tetrahydroanthraquinone having the general formula (II) with 1 to 100 parts by weight, per 100 parts by weight of said anthraquinone, of a weak basic non-reducing compound whereby during the course of the reaction the ring structure is oxidized and the nitro group is partially reduced to provide a product consisting essentially of a 1-hydroxylaminoanthraquinone.

17. A process for the preparation of 1-aminoanthraquinones comprising treating a 5-nitro-1,4,4a, 9a-tetrahydroanthraquinone having the general formula (II)

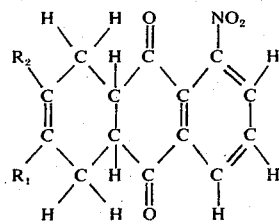

where, in the general formula, $R_1$ and $R_2$ individually represent a hydrogen atom or methyl group in a liquid medium with a basic reducing agent or a combination of a reducing agent and a basic compound whereby during the course of the reaction the ring structure is oxidized and the nitro group is reduced to provide a product consisting essentially of a 1-aminoanthraquinone.

18. The process of claim 17 wherein the basic reducing agent or reducing agent is a compound capable of reducing a nitro compound to an amino compound.

19. A process of claim 17 in which the reducing agent or basic reducing agent is used in an amount of 2 to 6 oxidationreduction equivalents per mole of the compound having the general formula II.

20. A process of claim 17 in which the reducing agent or basic reducing agent is at least one member selected from the group consisting of hydrogen sulfide, sulfides, disulfides, polysulfides, ammonia, elementary sulfur, metals, sugars, formaldehyde and oxalic acid.

21. A process of claim 20 in which the treatment is carried out at a temperature of 30° to 150°C.

22. A process of claim 21 in which the reduction of 1-hydroxylaminoanthraquinones is carried out in a reaction medium selected from the group consisting of aliphatic monohydric alcohols containing 1 to 4 carbon atoms and (di)ethyleneglycol monoalkyl ethers having the general formula $RO-CH_2CH_2\!-\!\!\left(OCH_2CH_2\right)_{\!n}\!OH$ wherein R is an alkyl group containing 1 to 8 carbon atoms and n is 0 or 1.

23. A process of claim 23 in which water is incorporated in the organic reaction medium in an amount as to provide the weight ratio of the organic reaction medium to the sum of the organic reaction medium and water of at least 0.2.

24. A process of claim 22 in which the organic reaction medium is used in an amount of about 4 times the weight of the 1-hydroxylaminoanthraquinone.

25. A process of claim 22 in which the organic reaction medium is used in an amount of 10 to 50 times the weight of the 1-hydroxylaminoanthraquinone.

26. A process for the preparation of 1-aminoanthraquinones comprising treating of 5-nitro-1,4,4a, 9a-tetrahydroanthraquinone in a liquid medium at a temperature of 0° to 200°C using 2 to 6 oxidation-reduction equivalents of a basic reducing agent per mole of the said antrhraquinone whereby during the course of the reaction the ring structure is oxidized and the nitro group is reduced to provide a product consisting essentially of 1-aminoanthraquinone.

27. A process for the prepara of 1-aminoanthraquinones comprising treating at a temperature of 0° to 200°C a 5-nitro-1,4,4a,9a-tetrahydroanthraquinone having the general formula (II) using 2 to 6 oxidation-reduction equivalents of a reducing agent per mole of said anthraquinone in the presence of a basic compound whereby during the course of the reaction the ring structure is oxidized and the nitro group is reduced to provide a product consisting essentially of a 1-aminoanthraquinone.

28. A process of claim 27 in which the treatment is carried out at a temperature of 30° to 150°C.

29. A process for the preparation of 1-aminoanthraquinones comprising treating a 5-nitro-1,4,4a, 9a-tetrahydroanthraquinone having the general formula (II)

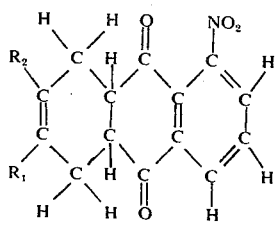

where, in the formula, $R_1$ and $R_2$ individually represent a hydrogen atom or methyl group
in a liquid medium with a basic compound to obtain an 1-hydroxylaminoanthraquinone and reducing said 1-hydroxyaminoanthraquinone into an 1-aminoanthraquinone whereby during the course of the reaction the ring structure is oxidized and the nitro group is reduced to provide a product consisting essentially of a 1-aminoanthraquinone.

30. A process of claim 29 in which the reduction of 1-hydroxylaminoanthraquinones is carried out at a temperature of 0° to 200°C.

31. A process of 29 in which the 1-hydroxylaminoanthraquinone is reduced in the presence of an aliphatic monohydric alcohol containing 1 to 4 carbon atoms by means of at least one metal selected from the group consisting of iron, nickel, zinc, magnesium and aluminum and a mineral acid.

32. A process of claim 31 in which the mineral acid is an acid selected from the group consisting of hydrochloric acid and sulfuric acid.

33. A process of claim 31 in which the reduction of 1-hydroxylaminoanthraquinone is carried out at a temperature of 50° to 150°C.

34. A process of claim 29 in which the 1-hydroxylaminoanthraquinone is reduced in the presence of an ethyleneglycol monoalkyl ether having the general formula $RO-CH_2-(OCH_2CH_2)_{\overline{n}}OH$ wherein R is an alkyl group containing 1 to 8 carbon atoms and $n$ is 0 or 1 by means of at least one metal selected from the group consisting of iron, nickel, zinc, magnesium and aluminum and a mineral acid.

35. A process of claim 34 in which the mineral acid is an acid selected from the group consisting of hydrochloric acid and sulfuric acid.

36. A process of claim 34 in which the reduction of 1-hydroxylaminoanthraquinone is carried out at a temperature of 50° to 150°C.

37. A process of claim 29 in which the 1-hydroxylaminoanthraquinone is reduced in the presence of an ethyleneglycol monoalkyl ether having the general formula $RO-CH_2CH_2-(OCH_2CH_2)_{\overline{n}}OH$ wherein R represents an alkyl group containing 1 to 8 carbon atoms and $n$ is 0 or 1, by means of gaseous hydrogen using a hydrogenation catalyst.

38. A process of claim 37 in which the reduction of 1-hydroxylaminoanthraquinone is carried out at a temperature of 20° to 150°C.

* * * * *